United States Patent [19]

Milner

[11] Patent Number: 5,304,659
[45] Date of Patent: Apr. 19, 1994

[54] PREPARATION OF POLYCYCLIC DYES

[75] Inventor: David J. Milner, Whitefield, England

[73] Assignee: Zeneca Limited, London, England

[21] Appl. No.: 57,806

[22] Filed: May 7, 1993

[30] Foreign Application Priority Data

May 7, 1992 [GB] United Kingdom ............... 9209870

[51] Int. Cl.$^5$ .......................................... C07D 307/77
[52] U.S. Cl. .................................... 549/299; 544/164; 546/300; 560/20; 564/434
[58] Field of Search .................. 549/299; 546/300; 544/164; 560/20; 564/434

[56] References Cited

U.S. PATENT DOCUMENTS 5,214,161  5/1993  Milner .................. 549/299

FOREIGN PATENT DOCUMENTS 252406  1/1988  European Pat. Off. .
436940  1/1990  European Pat. Off. .
518493  12/1992  European Pat. Off. .

OTHER PUBLICATIONS

Research Disclosure, No. 343, 10 Nov. 1992, Emsworth(G) 'Di:oxo-di:hydro:benzo-di:furan poly:cyclic dye'.

Primary Examiner—C. Warren Ivy
Assistant Examiner—A. Owens
Attorney, Agent, or Firm—Cushman, Darby & Cushman

[57] ABSTRACT

A process for the preparation of a polycyclic dye of Formula (1):

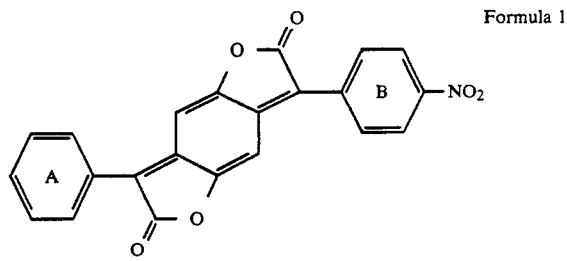

by reacting a compound of Formula (2):

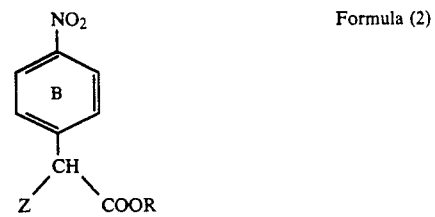

with a benzofuranone of the Formula (3):

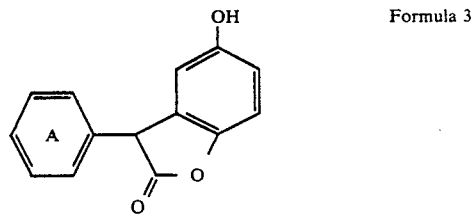

wherein:
Ring A is unsubstituted or is substituted by from one to three groups;
Ring B is unsubstituted, apart from the nitro group, or is substituted by one or two further groups;
R is H, optionally substituted alkyl or optionally substituted aryl; and
Z is an oxyammonium group, and certain novel compounds of Formula (2) are disclosed.

The process provides a convenient route to polycyclic dyes which are useful for the coloration of synthetic textile materials particularly polyesters.

5 Claims, No Drawings

PREPARATION OF POLYCYCLIC DYES

This invention relates to a process for the preparation of polycyclic dyes and to novel intermediates used in the process.

According to the present invention there is provided a process for the preparation of a polycyclic dye of Formula (1):

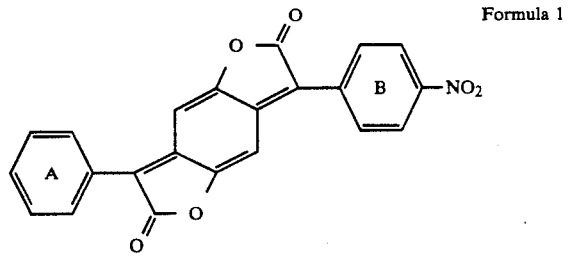

Formula 1 by reacting a compound of Formula (2):

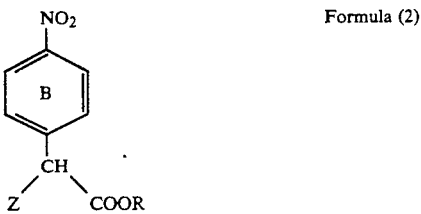

Formula (2)

with a benzofuranone of the Formula (3):

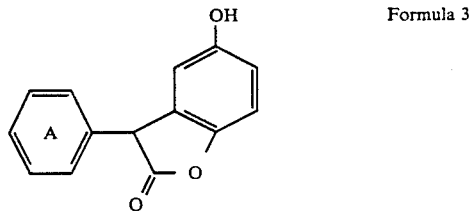

Formula 3 wherein:
Ring A is unsubstituted or is substituted by from one to three groups;
Ring B is unsubstituted, apart from the nitro group, or is substituted by one or two further groups;
R is H, optionally substituted alkyl or optionally substituted aryl; and
Z is an oxyammonium group.

Where Ring A carries substituents these are preferably in the 4-position, or in the 3- and 4-positions, or in the 3-, 4- and 5-positions.

Where Ring B carries substituents, in addition to the 4-nitro group, these are preferably in the 3-position, or in the 5-position, or in both the 3- and 5-positions.

Suitable substituent groups for Ring A may be independently selected from —NO₂; —OH; —CF₃; $C_{1-6}$-alkyl; $C_{3-4}$-alkenyl; halogen preferably —F, —Cl or —Br; —CN; —COOR¹ in which R¹ is —H or $C_{1-6}$-alkyl; —NR²R³ in which R² and R³ are each independently —H, $C_{1-6}$-alkyl or $C_{1-6}$-alkyl substituted by —OH, —$C_{1-4}$-alkoxy, phenyl, —CN or halogen; —NH-COR⁴; OR⁴; —OR⁴OR⁵; —OR⁴OR⁵OR⁶; —OR⁴-COR⁵; —OR⁴COOR⁵OR⁶; —OR⁴OCOR⁵; and —OR⁴OCOPh in which R⁴; R⁵ and R⁶ are each independently $C_{1-6}$-alkyl, preferably $C_{1-4}$-alkyl.

Suitable substituent groups for Ring B may be independently selected from any of the groups described above for Ring A and more preferably from $C_{1-4}$-alkyl, $C_{1-4}$-alkoxy and aryl-$C_{1-4}$-alkyl.

The alkyl groups defined as substituents for Ring A and Ring B may be straight or branched chain alkyl groups.

The oxyammonium group represented by Z and group R in the compound of Formula (2) are eliminated during the process and do not appear in the polycyclic dye of Formula (1), thus their precise identity is not important provided that they do not interfere with the reaction of the compound of Formula (2) with the compound of Formula (3).

The group R is preferably an optionally substituted alkyl group which provides the cheapest and simplest ester group —CO₂R. The alkyl group represented by R may be straight or branched and may carry one or more substituents such as $C_{1-4}$-alkoxy, phenyl, halo, especially chloro, bromo and fluoro. Examples of suitable alkyl groups represented by R are methyl, ethyl, chloromethyl, benzyl, methoxymethyl, ethoxymethyl and methoxyethyl. The oxyammonium group, Z, is preferably of Formula (4):

$$-O-NQ_3X^-$$  Formula (4)

wherein:
each Q independently is alkyl or aryl each of which may be optionally substituted, or two or three Q groups together with the nitrogen atom to which they are attached form a heterocyclic ring; and
X⁻ is halide.

Each Q independently is preferably $C_{1-6}$-alkyl, $C_{1-4}$-alkylphenyl or phenyl and more preferably methyl, ethyl, benzyl or phenyl or two or three Q groups together with the nitrogen to which they are attached preferably form a heteroalicyclic or heteroaromatic group such as pyridinium, morpholinium, piperidinium or piperazinium group. Where Q carries optional substituents these may be selected from any of the substituents described above for Rings A and B.

The halide represented by X⁻ is preferably chloride, bromide or iodide and more preferably chloride or bromide.

The oxyammonium group, Z, may be derived from a readily available amine oxide such as an aromatic, heterocyclic, alicyclic or aliphatic amine oxide e.g. a pyridine-N-oxide, a trialkylamine-N-oxide and N-alkylmorpholine-N-oxide, preferably a pyridine N-oxide. The amine oxide is preferably pyridine N-oxide which provides higher yields of the desired polycyclic dye of Formula (1).

The present process may be performed by stirring the reactants in a liquid medium, preferably in an acidic medium, more preferably in an acidic organic medium e.g. an alkylsulphonic acid such as methanesulphonic acid, or an alkylcarboxylic acid such as ethanoic acid, propanoic acid or butanoic acid, optionally containing another acid such as sulphuric acid, or in an organic liquid such as toluene or chlorobenzene which contains an acid preferably an alkylsulphonic acid such as methanesulphonic acid, an alkylcarboxylic acid such as ethanoic acid or an arylsulphonic acid such as toluene-sulphonic acid. The process is preferably carried out at a temperature from 0° C. to 150° C., more preferably from 10° C. to 100° C. and especially preferably from 15° C. to 50° C. When the reaction is substantially complete (as judged by disappearance of starting materials using a technique such as thin layer chromatography) the product may be isolated in any convenient manner. For example the product may be precipitated from the reaction mixture by addition of water, separated by filtration, washed with water and dried.

According to a further feature of the present invention there is provided a compound of Formula (2) wherein Ring B, R and Z are as hereinbefore defined.

It is preferred that in the compound of Formula (2) Ring B is unsubstituted or carries one or two substituents in the ortho positions with respect to the nitro group. Where Ring B carries one or two substituents these are preferably $C_{1-6}$-alkyl; $C_{1-6}$-alkoxy; $C_{3-4}$-alkenyl; phenyl; —$CO_2R$ in which R is as hereinbefore defined; or halogen such as Cl, Br or F.

The compound of Formula (2) may be prepared by reaction of a compound of Formula (5):

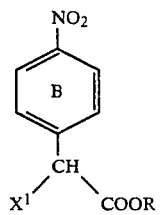

Formula (5)

wherein:

$X^1$ is halogen; and

Ring B and R are as hereinbefore defined with an amine N-oxide.

$X^1$ is preferably chlorine or bromine.

The amine N-oxide is preferably a heterocyclic N-oxide, such as pyridine N-oxide or N-methylmorpholine N-oxide or an aliphatic N-oxide such as trimethylamine N-oxide or triethylamine N-oxide.

The process may be performed by heating the reactants in a liquid medium, preferably in an organic liquid medium, more preferably in a halogenated liquid such as dichloromethane or 1,1,1-trichloro methane. The process is preferably carried out at a temperature from 30° C. to 150° C., more preferably from 40° C. to 120° C. and may be conveniently carried out in the liquid medium under reflux.

The compound of Formula (2) may be recovered from the reaction mixture by evaporation of the liquid and may be used without further purification in reaction with the compound of Formula (3).

The compound of Formula (3) may be prepared by reacting hydroquinone with a mandelic acid in 70% sulphuric acid or in acetic acid/sulphuric acid mixtures at elevated temperatures, the product may be recovered by filtration after diluting the reaction mixture with water.

The compound of Formula (5) may be prepared by reacting a nitrobenzene, having a vacant 4-position, with a dihaloethanoate in the presence of a base, such as an alkali metal alkoxide, in an aprotic liquid, such as dimethylformamide typically at temperatures from −60° C. to −10° C. The compound of Formula (5) may be isolated by neutralising the reaction mixture with an acid such as hydrochloric acid, extraction into an organic liquid and evaporation of the organic liquid to leave a residue which may be purified by distillation or column chromatography.

The compound of Formula (1) may be conveniently converted to the corresponding amino polycyclic dye using hydrogen and a platinium or palladium on carbon catalyst.

The compounds of Formula (1) and the amino derivatives are useful for the coloration of synthetic textile materials particularly polyesters.

The invention is further illustrated by the following examples in which all parts and percentages are by weight:

EXAMPLE 1

Preparation of
3-phenyl-7-(4-nitrophenyl)-2,5-dioxo-2,6-dihydrobenzo [1:2, 4:5-b']difuran Methyl 2-chloro-2-(4-nitrophenyl)ethanoate (2.3 parts), pyridine N-oxide (1.4 parts) and 1,1,1-trichloroethane (20 parts) were heated under reflux for 18 hours. The trichloroethane was removed from the reaction mixture to leave a sticky residue which solidified on standing.

The residue and 5-hydroxy-2-oxo-3-phenyl-2,3-dihydrobenzo furanone (1.1 parts) were stirred in methanesulphonic acid (10 parts) at 20°-25° C. for 3 days. The reaction mixture was poured into water and dried to give 3-phenyl-7-(4-nitrophenyl)-2,5-dioxo-2,6-dihydrobenzo [1:2-b, 4:5-b']difuran (0.6 parts, 40%)$\lambda_{max}$=464 nm ($CH_2Cl_2$).

EXAMPLE 2

Preparation of
3-phenyl-7-(3-methoxycarbonyl-4-nitrophenyl)-2,5-dioxo-2,6-dihydro[1:2-b, 4:5-b']difuran Methyl 2-chloro-2-(3-methoxycarbonyl-4-nitrophenyl)ethanoate (2.9 parts), pyridine N-oxide (1.4 parts) and 1,1,1-trichloroethane (15 parts) were heated under reflux for 18 hours. The trichloroethane was removed from the reaction mixture to leave a residue. The residue and 5-hydroxy-2-oxo-3-phenyl-2,3-dihydrobenzofuranone (2.3 parts) were stirred in methane sulphonic acid (10 parts) for 3 days. The reaction mixture was poured into water (300 parts), the precipitated solid was filtered off, washed with water and dried at 40° C. to give 3-phenyl-7-(3-methoxycarbonyl-4-nitrophenyl)-2,5-dioxo-2,6-dihydro [1:2-b, 4:5-b']difuran (2.3 parts, 52%)$\lambda_{max}$=462 nm ($CH_2Cl_2$).

EXAMPLE 3

Preparation of
3-phenyl-7-(4-nitro-3-phenylphenyl)-2,5-dioxo-2,6-dihydrobenzo[1:2, 4:5-b']difuran Methyl 2-chloro-2-(4-nitro-3-phenylphenyl)ethanoate (6.1 parts), pyridine N-oxide (3.0 parts) and 1,1,1-trichloroethane (30 parts) were heated under reflux for 20 hours. The trichloroethane was removed from the reaction mixture to leave a residue.

The residue and 5-hydroxy-2-oxo-3-phenyl-2,3-dihydrobenzofuranone (4.5 parts) were stirred in methane sulphonic acid (25 parts) at 20°-25° C. for 3 days. The reaction mixture was poured into water (500 parts) and dried to give 3-phenyl-7-(4-nitro-3-phenylphenyl)-2,5-dioxo-2,6-dihydrobenzo[1:2-b, 4:5-b']difuran (8.8 parts, 95%)$\lambda_{max}$=462 nm ($CH_2Cl_2$).

EXAMPLE 4

Preparation of 3-phenyl-7-(3-methoxy-4-nitrophenyl)-2,5-dioxo-2,6-dihydrobenzo[1:2, 4:5-b']difuran Methyl 2-chloro-2-(3-methoxy-4-nitrophenyl)ethanoate (2.3 parts), pyridine N-oxide (1.4 parts) and toluene (15 parts) were heated under reflux for 5 hours. The toluene was removed under vacuum from the reaction mixture to leave a residue.

The residue and 5-hydroxy-2-oxo-3-phenyl-2,3-dihydrobenzofuranone (2.3 parts) were stirred in methane sulphonic acid (5 parts) at 20°-25° C. for 4 days. The reaction mixture was poured into water and dried to give 3-phenyl-7-(3-methoxy-4-nitrophenyl)-2,5-dioxo-2,6-dihydrobenzo[1:2-b, 4:5-b']difuran (2.3 parts, 55%)$\lambda_{max}$=465 nm ($CH_2Cl_2$).

EXAMPLE 5

Preparation of 3-phenyl-7-(3-chloro-4-nitrophenyl)-2,5-dioxo-2,6-dihydrobenzo[1:2, 4:5-b']difuran Methyl 2-chloro-2-(3-chloro-4-nitrophenyl)ethanoate (2.6 parts), pyridine N-oxide (1.4 parts) and toluene (15 parts) were heated under reflux for 5 hours. The toluene was removed under vacuum from the reaction mixture to leave a residue.

The residue and 5-hydroxy-2-oxo-3-phenyl-2,3-dihydrobenzofuranone (2.3 parts) were stirred in methane sulphonic acid (5 parts) at 20°-25° C. for 4 days. The reaction mixture was poured into water and dried to give 3-phenyl-7-(3-chloro-4-nitrophenyl)-2,5-dioxo-2,6-dihydrobenzo[1:2-b, 4:5-b']difuran (2.4 parts, 57%)$\lambda_{max}$=464 nm ($CH_2Cl_2$).

EXAMPLE 6

Preparation of 3-phenyl-7-(4-nitrophenyl)-2,5-dioxo-2,6-dihydrobenzo[1:2, 4:5-b']difuran Methyl 2-chloro-2-(4-nitrophenyl)ethanoate (0.23 parts), trimethylamine N-oxide dihydrate (0.16 parts) and toluene (10 parts) were heated under reflux for 18 hours. The toluene was removed under vacuum from the reaction mixture to leave a residue.

The residue and 5-hydroxy-2-oxo-3-phenyl-2,3-dihydrobenzofuranone (0.2 parts) were stirred in methane sulphonic acid (5 parts) at 20°-25° C. for 3 days. The reaction mixture was poured into water and dried to give 3-phenyl-7-(4-nitrophenyl)-2,5-dioxo-2,6-dihydrobenzo[1:2-b, 4:5-b']difuran (0.05 parts, 12%)$\lambda_{max}$=464 nm ($CH_2Cl_2$).

EXAMPLE 7

Preparation of 3-phenyl-7-(4-nitrophenyl)-2,5-dioxo-2,6-dihydrobenzo[1:2, 4:5-b']difuran Methyl 2-chloro-2-(4-nitrophenyl)ethanoate (0.23 parts), N-methyl morpholine N-oxide (0.16 parts) and toluene (10 parts) were heated under reflux for 18 hours. The toluene was removed under vacuum from the reaction mixture to leave a residue.

The residue and 5-hydroxy-2-oxo-3-phenyl-2,3-dihydrobenzofuranone (0.2 parts) were stirred in methane sulphonic acid (10 parts) at 20°-25° C. for 3 days. The reaction mixture was poured into water and dried to give 3-phenyl-7-(4-nitrophenyl)-2,5-dioxo-2,6-dihydrobenzo[1:2-b, 4:5-b']difuran (0.04 parts, 10%)$\lambda_{max}$=465 nm ($CH_2Cl_2$).

I claim:

1. A process for the preparation of a polycyclic dye of Formula (1):

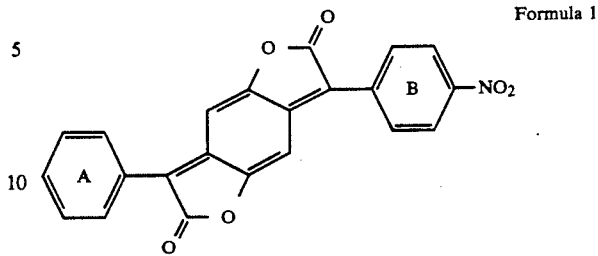

Formula 1 by reacting a compound of Formula (2):

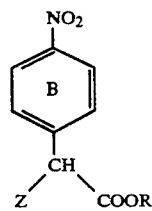

Formula (2)

with a benzofuranone of the Formula (3):

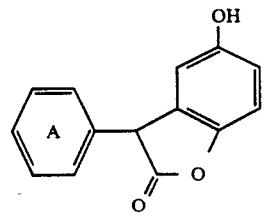

Formula 3 wherein:
- Ring A is unsubstituted or is substituted by from one to three groups;
- Ring B is unsubstituted, apart from the nitro group, or is substituted by one or two further groups;
- R is H, optionally substituted alkyl or optionally substituted aryl; and
- Z is an oxyammonium group.

2. A process according to claim 1 wherein the oxyammonium group, Z, is derived from an aromatic, heterocyclic, alicyclic or aliphatic amine oxide.

3. A process according to claim 1 or claim 2 wherein the oxyammonium group, Z, is derived from a pyridine N-oxide.

4. A compound of Formula 2:

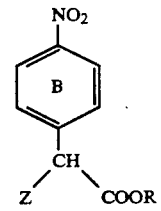

Formula (2)

wherein:
- Ring B is unsubstituted, apart from the nitro group, or is substituted by one or two further groups;
- R is H, optionally substituted alkyl or optionally substituted aryl; and
- Z is an oxyammonium group.

5. A compound according to claim 4 wherein the oxyammonium group, Z, is derived from an aromatic, heterocyclic, alicyclic or aliphatic amine oxide.

* * * * *